US00PP25868P2

(12) United States Plant Patent
Vloten

(10) Patent No.: US PP25,868 P2
(45) Date of Patent: Sep. 8, 2015

(54) ***THUJA* PLANT NAMED 'ANNA VAN VLOTEN'**

(50) Latin Name: *Thuja occidentalis*
Varietal Denomination: Anna van Vloten

(71) Applicant: Casey van Vloten, Abbotsford (CA)

(72) Inventor: Casey van Vloten, Abbotsford (CA)

(73) Assignee: Spring Meadow Nursery Inc., Grand Haven, MI (US)

( * ) Notice: Subject to any disclaimer, the term of this patent is extended or adjusted under 35 U.S.C. 154(b) by 24 days.

(21) Appl. No.: 13/987,825

(22) Filed: Sep. 7, 2013

(51) Int. Cl.
*A01H 7/00* (2006.01)

(52) U.S. Cl.
USPC ..... Plt./213

(58) Field of Classification Search
USPC ..... Plt./213
See application file for complete search history.

(56) References Cited

PUBLICATIONS

Springmeadownursery.com/plant/83910; *Thuja occidentalis* 'Anna Van Vloten', 2010.*

* cited by examiner

*Primary Examiner* — Anne Grunberg
(74) *Attorney, Agent, or Firm* — C. A. Whealy

(57) ABSTRACT

A new and distinct cultivar of *Thuja* plant named 'Anna van Vloten', characterized by its compact and upright plant habit; rounded plant form; moderately vigorous growth habit; moderate growth rate; dense and bushy form; bright yellow green-colored leaves; bright yellow green coloration maintained during the winter; and good winter hardiness and wind resistance.

1 Drawing Sheet

Botanical designation: *Thuja occidentalis.*
Cultivar denomination: 'ANNA van VLOTEN'.

BACKGROUND OF THE INVENTION

The present invention relates to a new and distinct cultivar of *Thuja* plant, botanically known as *Thuja occidentalis*, commonly known as American Arborvitae and hereinafter referred to by the name 'Anna van Vloten'.

The new *Thuja* plant is a naturally-occurring branch mutation of *Thuja occidentalis* 'Danica', not patented. The new *Thuja* plant was discovered and selected by the Inventor in 1993 on a single plant of 'Danica' in a controlled outdoor nursery environment in Abbotsford, British Columbia, Canada.

Asexual reproduction of the new *Thuja* plant by hardwood cuttings in a controlled environment in Abbotsford, British Columbia, Canada since October, 2000 has shown that the unique features of this new *Thuja* plant are stable and reproduced true to type in successive generations.

SUMMARY OF THE INVENTION

Plants of the new *Thuja* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Anna van Vloten'. These characteristics in combination distinguish 'Anna van Vloten' as a new and distinct *Thuja* plant:

1. Compact and upright plant habit; rounded plant form.
2. Moderately vigorous growth habit; moderate growth rate.

3. Dense and bushy form.
4. Bright yellow green-colored leaves; bright yellow green coloration maintained during the winter.
5. Good winter hardiness and wind resistance.

Plants of the new *Thuja* can be compared to plants of the female parent, 'Danica'. Plants of the new *Thuja* differ primarily from plants of 'Danica' in the leaf color as plants of 'Danica' have green-colored leaves.

Plants of the new *Thuja* can be compared to plants of *Thuja occidentalis*, 'Filips Magic Moment', disclosed in U.S. Plant Pat. No. 21,974. In side-by-side comparisons conducted in Abbotsford, British Columbia, Canada, plants of the new *Thuja* differed primarily from plants of 'Filips Magic Moment' in the following characteristics:

1. Plants of the new *Thuja* were rounded in plant form whereas plants of 'Filips Magic Moment' were conical in plant form.
2. Plants of the new *Thuja* were more vigorous than plants of 'Filips Magic Moment'.

BRIEF DESCRIPTION OF THE PHOTOGRAPH

The accompanying colored photograph illustrates the overall appearance of the new *Thuja* plant showing the colors as true as it is reasonably possible to obtain in colored reproductions of this type. Colors in the photograph may differ slightly from the color values cited in the detailed botanical description which accurately describe the colors of the new *Thuja* plant.

The photograph comprises a side perspective view of a typical plant of 'Anna van Vloten'.

DETAILED BOTANICAL DESCRIPTION

The aforementioned photograph and following observations, measurements and values describe plants grown during the summer in ground beds in an outdoor nursery in Grand Haven, Mich. and under cultural practices typical of commercial *Thuja* plant production. Plants were two years old when the photograph and description were taken. In the following detailed description, color references are made to The Royal Horticultural Society Colour Chart, 2001 Edition, except where general terms of ordinary dictionary significance are used.

Botanical classification: *Thuja occidentalis* 'Anna van Vloten'.

Parentage: Naturally-occurring branch mutation of *Thuja occidentalis* 'Danica', not patented.

Propagation:

*Type*.—By hardwood cuttings.

*Time to initiate roots, winter*.—About five months at temperatures about 18° C.

*Time to produce rooted young plants, winter*.—About two years at temperatures about 20° C.

*Root description*.—Fine, fibrous; brown and white in color.

*Rooting habit*.—Freely branching; dense.

Plant description:

*Plant and growth habit*.—Perennial evergreen shrub; compact and upright plant habit and rounded plant form; moderately vigorous growth habit; moderate growth rate.

*Plant height*.—About 22 cm.

*Plant diameter, base*.—About 46 cm.

*Branching habit*.—Freely branching habit with about 25 lateral branches developing per plant; dense and bushy habit.

*Lateral branch description*.—Length: About 15 cm. Diameter: About 3 mm. Internode length: About 2 cm. Aspect: Lateral branches about 20° to 30° from stem axis. Strength: Strong. Texture, developing branches: Scaly; glabrous. Texture, main trunk: Woody. Color: Close to 200A.

*Leaf description*.—Appearance and arrangement: Flattened and closely appressed, scale-like; opposite, simple; sessile. Length: About 3 mm. Width: About 2 mm. Shape: Ovate. Apex: Acute. Base: Obtuse. Margin: Entire. Venation pattern: Parallel. Texture: Smooth, glabrous. Fragrance: Aromatic and cedar-like. Color: Developing leaves, upper and lower surfaces: Close to 151B. Fully expanded leaves, upper and lower surfaces: Close to 138A; venation, close to 138A; during the winter, main color becoming closer to 146B with apices, close to 153B and margins, close to 168B; leaves do not turn brown during the winter similar to other varieties of *Thuja occidentalis* known to the Inventor.

Cone description: Cone development has not been observed on plants of the new *Thuja*.

Garden performance: Plants of the new *Thuja* have been observed have good garden performance, good winter hardiness, to be wind-tolerant and to tolerate temperatures ranging from about −20° C. to about 35° C.

Pathogen & pest resistance: Plants of the new *Thuja* have been not been observed to be resistant to pathogens and pests common to *Thuja* plants.

It is claimed:

1. A new and distinct *Thuja* plant named 'Anna van Vloten' as illustrated and described.

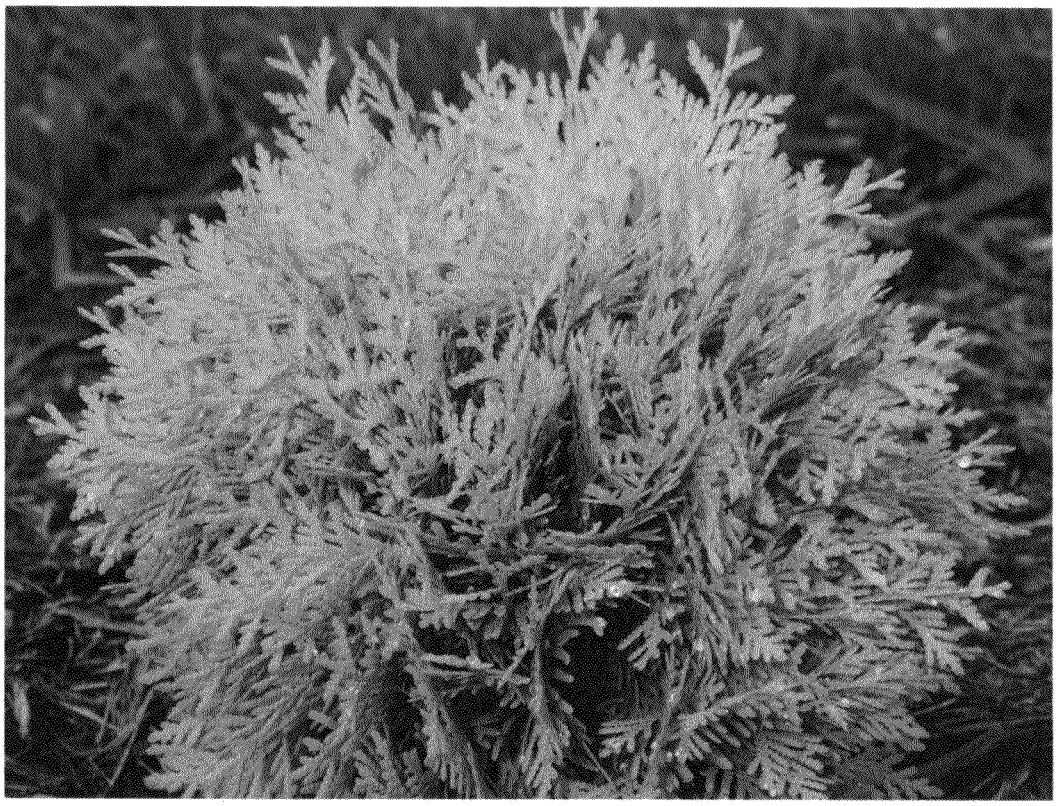

* * * * *